United States Patent [19]

Seto et al.

[11] Patent Number: 4,839,361

[45] Date of Patent: * Jun. 13, 1989

[54] DIHYDROPYRIDINE-5-PHOSPHONIC ACID CYCLIC PROPYLENE ESTER

[75] Inventors: Kiyotomo Seto, Funabashi; Sakuya Tanaka, Hasuda; Ryozo Sakoda, Kashiwa, all of

[73] Assignee: Nissan Chemical Industries Ltd., Tokyo, Japan

[*] Notice: The portion of the term of this patent subsequent to Mar. 18, 2003 has been disclaimed.

[21] Appl. No.: 792,981

[22] Filed: Oct. 30, 1985

Related U.S. Application Data

[63] Continuation-in-part of Ser. No. 654,473, Sep. 26, 1984, Pat. No. 4,576,934.

[30] Foreign Application Priority Data

Sep. 26, 1983 [JP] Japan .................................. 58-177710
Aug. 3, 1984 [JP] Japan .................................. 59-163649

[51] Int. Cl.$^4$ .................... C07D 401/12; A61K 31/44
[52] U.S. Cl. .................................... 514/252; 544/337
[58] Field of Search ............... 544/337, 365; 546/321, 546/21

[56] References Cited

U.S. PATENT DOCUMENTS 4,423,052 12/1983 Araki et al. ..................... 546/321
4,576,934 3/1986 Seto et al. ....................... 546/21

FOREIGN PATENT DOCUMENTS 150040 10/1985 European Pat. Off. .

Primary Examiner—Jane T. Fan
Attorney, Agent, or Firm—Oblon, Spivak, McClelland, Maier & Neustadt

[57] ABSTRACT

A compound of the formula:

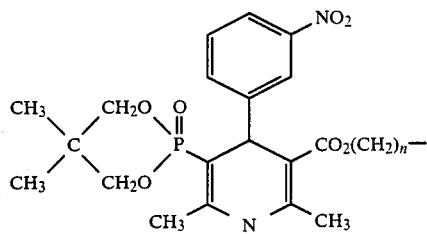

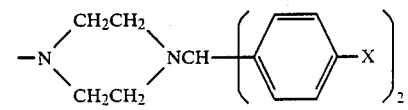

wherein X is hydrogen or fluorine and n is 2 or 3; or its pharmaceutically acceptable salt.

9 Claims, No Drawings

DIHYDROPYRIDINE-5-PHOSPHONIC ACID CYCLIC PROPYLENE ESTER

This is a continuation-in-part of U.S. patent application No. 654,473 filed 9/26/84 now U.S. Pat. No. 4,576,934 issued 3/18/86.

BACKGROUND OF THE INVENTION

1. Field of the Invention

The present invention relates to a novel 1,4-dihydropyridine-5-phosphonic acid cyclic propylene ester, a process for the preparation thereof, and an antihypertensive agent or coronary or peripheral vasodilator composition containing the novel ester or its pharmaceutically acceptable salt.

2. Description of the Prior Art 1,4-Dihydropyridines are known to be useful for the medical treatment of coronary heart diseases, cerebral diseases, hypertension or arrhythmia, as they are capable of inhibiting the contraction of smooth muscle and cardiac muscle by calcium antagonistic effects (see A. Fleckenstein, Annu. Rev. Pharmacol. Toxicol., 17, 149–166 (1977)). However, the majority of 1,4-dihydropyridines known or being developed are substituted at the 3- and 5-positions by a carboxylic acid ester group.

Dihydropyridine-5-phosphonate derivatives are disclosed in prior art references. However, none of them suggests or indicates the specific compounds of the present invention.

RELEVANT REFERENCES ARE AS FOLLOWS

A. I. Razumov et al. synthesized a dihydropyridine-4-alkyl-5-phosphonate derivative (Zh. Obshch. Khim., 47, 1190–1191 (1977) and ibid., 51, 547–552 (1981)). Further, Von K. Issleib et al. synthesized 1,4-dihydropyridine-4-aryl-5-phosphonates (more specifically, diethyl 2,6-dimethyl-4-phenyl-3-ethoxy carbonyl-1,4-dihydropyridine-5-phosphonate and diethyl 2,6-dimethyl-4-(4-methoxyphenyl)-3-ethoxy carbonyl-1,4-dihydropyridine-5-phosphonate) (J. Prakt. Chem., Vol. 318, 207–220 (1976)). None of these references indicates the pharmacological activities. Furthermore, U.K. Patent Application GB 2105989A discloses a wide range of 1,4-dihydropyridine-5-phosphonate derivatives by a general formula, and teaches that the compounds represented by the general formula have cardiac activities. However, the specification of this Patent Application discloses no actual examples for the syntheses of 1,4-dihydropyridine-5-phosphonate derivatives and no pharmacological data relating to such derivatives.

SUMMARY OF THE INVENTION

The present invention provides a novel compound represented by the formula:

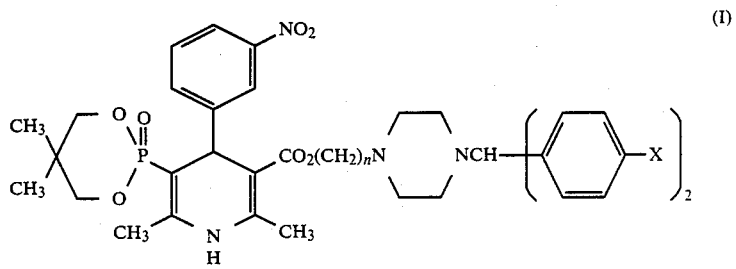

(I)

wherein X is hydrogen or fluorine and n is 2 or 3, or its pharmaceutically acceptable salt.

Some of the compounds of the formula I have optical isomers of diastereomers. The present invention covers such optical isomers and diastereomers.

The present invention also provides an antihypertensive agent or coronary or peripheral vasodilator composition comprising an effective amount of the compound of the formula I or its pharmaceutically acceptable salt and a pharmaceutically acceptable diluent or carrier.

DESCRIPTION OF THE PREFERRED EMBODIMENT

The compounds of the present invention can be prepared in accordance with the flow chart of the following Scheme 1.

Scheme 1

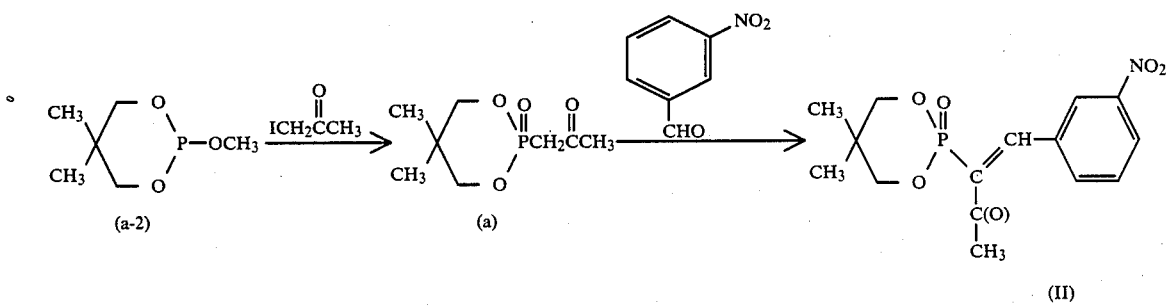

-continued
Scheme 1

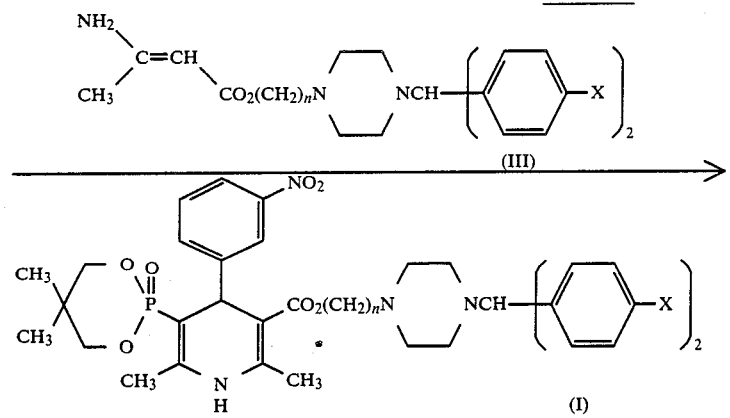

In Scheme 1, n and X have the same meanings as defined with respect to the formula I.

The acetonyl phosphonic acid cyclic propylene ester (a) can be prepared by means of a conventional technique (see D. W. White, J. Am. Chem. Soc., 92, 7125–7135 (1970)). Namely, as shown by Scheme 1, it is obtainable by the reaction of a 1-methoxy-4,4-dimethyl-1-phosha-2,6-dioxacyclohexane derivative (a-2) with iodoacetone.

The compounds of the present invention of the formula I can be obtained by reacting the compound of the formula II with the compound of the formula III in an inert solvent in accordance with the above Scheme 1. The starting compound of the formula II is obtainable by reacting the acetonyl phosphonic acid cyclic ester (a) with m-nitro-benzaldehyde by means of a conventional technique. Likewise, the starting compound of the formula III can readily be obtained by reacting the corresponding carbonyl compound with ammonia. The starting compound of the formula III may be formed in the reaction system simply by mixing the corresponding carbonyl compound with ammonia and is not necessarily required to be isolated.

The inert solvent includes an alcohol solvent such as methanol, ethanol, propanol or isopropanol, an ether solvent such as 1,2-dimethoxyethane or THF, an aromatic hydrocarbon solvent such as benzene, toluene or xylene, a nitrile solvent such as acetonitrile or benzonitrile, an amide solvent such as DAM, DMF or N-methylpyrrolidone, a sulfoxide solvent such as DMSO or sulfolane, an ester solvent such as ethyl acetate or butyrolactone, or pyridine.

The reaction is usually conducted at a temperature of from room temperature to 200° C., preferably from 60° to 140° C., for from 1 to 100 hours, preferably from 5 to 20 hours.

As mentioned above, the compounds of the present invention are not only capable of inhibiting the contraction of smooth muscle and cardiac muscle by the calcium antagonistic effects but also antihypertensively effective when administered orally. Thus, they are useful for the medical treatment of the coronary heart diseases, cerebral diseases or hypertension of mammals.

Thus, the present invention provides an anti-hypertensive agent or coronary or peripheral vasodilator composition comprising an effective amount of the compound of the formula I or its phamaceutically acceptable salt, and a pharmaceutically acceptable diluent or carrier. Such a composition may also be formulated into a veterinary composition by combining the compound of the present invention with a veterinarily acceptable diluent or carrier.

Such compositions may be used in the form suitable for oral administration, e.g. tablets or capsules, in the form suitable for transdermal administration, e.g. ointments or plasters, in the form suitable for inhalation, e.g. aerosols or solutions suitable for spraying, in the form suitable for injection administration, e.g. a sterilized aqueous solution, or in the form of a suppository suitable for use in anus, vagina or rectum.

The compositions of the present invention usually contain the compound of the formula I in an amount of from about 0.1 to about 99.5% by weight, preferably from about 0.5 to about 95% by weight, based on the total weight of the composition.

The compounds of the present invention or the compositions of the present invention may be used in combination with other pharmaceutically or veterinarily active compounds. Further, the composition of the present invention may contain a plurality of the compounds of the formula I.

The daily dose of the compounds of the formula I may be varied depending upon the type and the condition of the desease to be cured and the type of the patient (the age, sex, sensitivity, etc.). In the case of the intravenous administration, the daily dose is usually from 0.0001 to 10 mg, preferably from 0.0005 to 1 mg, of the active ingredient per 1 kg of the body weight. Likewise, in the case of the oral or transdermal administration, the daily dose is usually from 0.001 to 100 mg of the active ingredient per 1 kg of the body weight. Further, the daily dose in the case of the administration in the form of a suppository to e.g. a vagina or rectum, is usually from 0.001 to 200 mg, preferably from 0.005 to 100 mg, of the active ingredient per 1 kg of the body weight. The content of the active ingredient in an aerosol, is usually from 0.1 to 10% by weight, preferably from 0.1 to 2% by weight. Such a daily dose may be divided for administration twice or more times per day.

The above-mentioned compositions containing the compounds of the formula I may be prepared by a conventional method, and a conventional excipient may be incorporated therein.

The present invention will be now described in further detail with reference to Working Examples, Test Examples and various formulations. However, it should

EXAMPLES be understood that the present invention is by no means restricted by these specific Examples.

Test 1: Pharmacological activities of the compounds of the present invention.

(1) Calcium antagonistic effects 10 mm in situ length of taenia caecum of guinea pig was suspended at a tension of 1 g in a 20 ml organ bath filled with a physiological salt solution (NaCl: 135 mM, KCl: 5 mM etc.).

This solution was bubbled with a gas mixture of 95% $O_2$-5% $CO_2$ and kept at 37° C. Then, the preparation was depolarized by a $K^+$ rich solution (NaCl: 40 mM, KCl: 100 mM). After 10–20 minutes equilibration period, 10 mM of $CaCl_2$ was added to the bathing solution. The contraction was produced, and then the test compound applied cumulatively. The relaxation produced was expressed as percentage of the maximum relaxation produced by $10^{-4}$M papaverine, and the concentration of the compound producing 50% relaxation, i.e. $ID_{50}$ (M), was calculated. The values of $pID_{50}$ ($pID_{50} = -\log [ID_{50}]$, are summarized in Table 3.

(2) Antihypertensive effects

After oral administration of the test compound dissolved in a $H_2O$-PEG 400 solvent mixture ($H_2O$:PEG 400 (w/w)=1:3) to the male spontaneously hypertensive rat (SHR), the systolic blood pressure was measured by a tail cuff method. Prior to the measurement, rats were warmed at 50° C. for five minutes. The results are summarized in Table 3.

TABLE 3
Calcium antagonistic effects and antihypertensive effects of the compounds of the present invention.

| Compounds | $pID_{50}$ | Antihypertensive effects Dose (mg/kg) | Maximum decrease(%) |
|---|---|---|---|
| Hydrochloride of Example 1 | 7.63 | 20 | 40 |
| Hydrochloride of Example 2 | 7.53 | 20 | 31 |
| Hydrochloride of Example 3 | 7.39 | 20 | 39 |
| Hydrochloride of Example 4 | 7.20 | 20 | 22 |

Test 2: Acute toxicity test.

ddY mice (♂, 4 weeks old) were divided into groups of five mice and the test compound dissolved in purified water was administered orally (5% solution) (p.o) or intraperitoneally (1% solution) (i.p) to the male ddY mice.

After seven days, $LD_{50}$ values were calculated from the dead rats recorded in the individual dosage groups by the method of Litchfield-Wilcoxon. The results are shown in Table 4.

TABLE 4

| Tested compound | $LD_{50}$ (mg/kg) i.p. | p.o. |
|---|---|---|
| Hydrochloride of the Compound of Example 1 | 163 | 194 |

EXAMPLE 1

Synthesis of β-(4-diphenylmethyl-1-piperazinyl)-ethyl 5-(4,4-dimethyl-1-oxo-1-phospha-2,6-dioxacyclohexa-1-yl)-2,6-dimethyl-1,4-dihydro-4-(3-nitrophenyl)-pyridine-3-carboxylate 1.44 g of β-(4-diphenylmethyl-1-piperazinyl)-ethyl 3-aminocrotonate and 1.29 g of 1-(α-acetyl-3-nitrostyryl)-4,4-dimethyl-1-oxo-1-phospha-2,6-dioxacyclohexane were dissolved in 20 ml of toluene, and the solution was refluxed for 9 hours. Then, the solvent was distilled off under reduced pressure, and the residue was subjected to silica gel column chromatography by using 10% ethanol-ethyl acetate as the developer. The fraction containing the desired substance was distilled under reduced pressure to remove the solvent, whereby the above-identified compound was obtained.

In a similar manner, compounds of Examples 2 to 4 were obtained. The characteristics of the compounds thus obtained are shown in Table 1, and their spectral data are shown in Table 2.

TABLE 1
Compounds of Example 1 to 4 and their characteristics

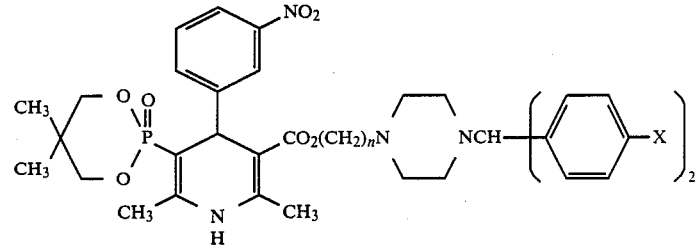

(I)

| Example No. | n | X | Yield (%) | Characteristics |
|---|---|---|---|---|
| 1 | 2 | H | 56 | Yellow oily Substance |
| 2 | 3 | H | 49 | Yellow oily Substance |
| 3 | 2 | F | 62 | Yellow oily Substance |
| 4 | 3 | F | 46 | Yellow oily Substance |

TABLE 2
Compounds of Example 1 to 4 and their spectral data

| Example No. | NMR Spectrum δ-value (in $CDCl_3$) | Mass spectrum m/e (intensity ratio) |
|---|---|---|
| 1 | 8.20–7.05(14H,m),4.85(1H,d,J=11Hz) 4.50–3.20(7H,m),2.85–2.10(16H,m), 0.97(6H,d,J=9Hz) | 167 (100) 246 (28) 683 (10) |
| 2 | 8.20–7.00(14H,m),4.83(1H,d,J=11Hz) 4.40–3.30(7H,m),2.75–1.50(18H,m), 0.98(6H,d,J=9Hz) | 167 (100) 300 (23) 697 (32) 714 (2,M+) |
| 3 | 8.10–6.73(12H,m),4.85(1H,d,J=11Hz) 4.40–3.30(7H,m),2.80–2.05(16H,m), | 203 (96) 300 (32) |

TABLE 2-continued

Compounds of Example 1 to 4 and their spectral data

| Example No. | NMR Spectrum δ-value (in CDCl$_3$) | Mass spectrum m/e (intensity ratio) |
|---|---|---|
| | 0.98(6H,d,J=6Hz) | 719 (100) |
| | | 736 (18,M$^+$) |
| 4 | 8.10–6.65(12H,m),4.83(1H,d,J=11Hz) | 203 (100) |
| | 4.40–3.30(7H,m),2.65–1.50(18H,m), | 733 (49) |
| | 0.98(6H,d,J=8Hz) | 750 (3,M$^+$) |

Now, examples will be given for various formulations containing the compound of the formula I.

Tablets

Composition (1,000 tablets)

| Hydrochloride of the compound of the Example 1 | 5.0 (g) |
|---|---|
| Lactose | 190.0 |
| Corn starch | 75.0 |
| Crystal cellulose powder | 25.0 |
| Methyl cellulose | 3.0 |
| Magnesium stearate | 2.0 |
| | 300.0 |

The above ingredients in the respective amounts were introduced into a twin shell mixer and uniformly mixed. This powder mixture was tableted by a direct compression method to obtain tablets having a weight of 300 mg per tablet.

Capsules

Composition (1,000 capsules)

| Hydrochloride of the Compound of the Example 1 | 5 (g) |
|---|---|
| Corn starch | 145 |
| Crystal cellulose powder | 145 |
| Magnesium stearate | 5 |
| | 300 |

The above ingredients in the respective amounts were introduced into a twin shell mixer and uniformly mixed. This powder mixture was packed in hard gelatin capsules in an amount of 300 mg per capsule.

Powder

Composition:

| Hydrochloride of the compound of the Example 1 | 1.0 (g) |
|---|---|
| Lactose | 88.0 |
| Crystal cellulose powder | 10.0 |
| Methyl cellulose | 1.0 |
| | 100.0 |

The above ingredients in the respective amounts were introduced into a twin shell mixer and uniformly mixed to obtain a powder.

Syrup

Composition (2% syrup):

| Hydrochloride of the compound of the Example 1 | 2.0 (g) |
|---|---|
| Sugar | 30.0 |
| Glycerin | 5.0 |
| Flavoring agent | 0.1 |
| 96% ethanol | 10.0 |
| Methyl p-hydroxybenzoate | 0.03 |
| Purified water to make | 100.0 g |

The sugar and the hydrochloride of the compound of Example 1 were dissolved in 60 g of warm water, and after cooling the solution, a solution of the flavoring agent in glycerin and ethanol was added. Then, water was added to this mixture to bring the total amount to 100.0 g.

What is claimed is:

1. A compound of the formula:

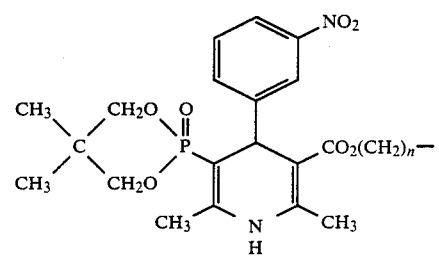

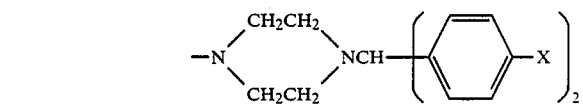

wherein X is hydrogen or fluorine and n is 2 or 3; or its pharmaceutically acceptable salt.

2. The compound of claim 1, wherein n is 2.
3. The compound of claim 1, wherein n is 3.
4. The compound of claim 1, wherein X is hydrogen.
5. The compound of claim 1, wherein X is fluorine.
6. An antihypertensive, coronary or peripheral vasodilator composition comprising
   (a) an antihypertensive, coronary or peripheral vasodilator effective amount of the compound of claim 1; and
   (b) a pharmaceutically acceptable diluent or carrier.
7. A method of treating hypertension in a subject in need of such treatment comprising administering to the subject an antihypertensive effective amount of the compound of claim 1 to produce such effect.
8. A method of producing coronary vasodilation in a patient in need of such treatment comprising administering to the patinent a coronary vasodilating effective amount of the compound of claim 1 to produce such effect.
9. A method of producing peripheral vasodilation in a patient in need of such treatment comprising administering to the patient a peripheral vasodilating effective amount of the compound of claim 1 to produce such effect.

* * * * *